(12) United States Patent
Chua (10) Patent No.: US 9,814,854 B2
(45) Date of Patent: Nov. 14, 2017

(54) METHOD AND SYSTEM WITH DIVIDED CANNULA HAVING LOW OXYGEN FLOW RATE AND IMPROVED END-TIDAL $CO_2$ MEASUREMENT

(71) Applicant: SALTER LABS, Arvin, CA (US)

(72) Inventor: James Chua, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 605 days.

(21) Appl. No.: 14/212,118

(22) Filed: Mar. 14, 2014

(65) Prior Publication Data

US 2014/0276169 A1 Sep. 18, 2014

Related U.S. Application Data

(60) Provisional application No. 61/792,007, filed on Mar. 15, 2013.

(51) Int. Cl.
| | | |
|---|---|---|
| *A61M 16/06* | (2006.01) | |
| *A61B 5/08* | (2006.01) | |
| *A61B 5/097* | (2006.01) | |
| *A61B 5/083* | (2006.01) | |
| *A61M 16/20* | (2006.01) | |
| *A61M 16/08* | (2006.01) | |

(52) U.S. Cl.
CPC ....... *A61M 16/0672* (2014.02); *A61B 5/0836* (2013.01); *A61B 5/097* (2013.01); *A61M 16/0677* (2014.02); *A61M 16/085* (2014.02); *A61M 16/208* (2013.01); *A61M 2202/0208* (2013.01); *A61M 2230/432* (2013.01)

(58) Field of Classification Search
CPC .......... A61M 16/0666; A61M 16/0672; A61M 16/0677; A61B 5/0836; A61B 5/097
See application file for complete search history.

(56) References Cited

U.S. PATENT DOCUMENTS

| | | | |
|---|---|---|---|
| 5,335,656 | A | 8/1994 | Bowe et al. |
| 5,626,131 | A | 5/1997 | Chua et al. |
| 5,697,364 | A | 12/1997 | Chua et al. |
| 5,735,268 | A | 4/1998 | Chua et al. |
| 6,655,385 | B1 | 12/2003 | Curti et al. |

(Continued)

OTHER PUBLICATIONS

International Search Report Corresponding to PCT/US2014/027996 dated Jul. 4, 2014 3 pages.

*Primary Examiner* — Valerie L Woodward
(74) *Attorney, Agent, or Firm* — Davis & Bujold, PLLC; Michael J. Bujold (57) ABSTRACT

A nasal cannula having a face piece including first and second nares which each communicate with a respective nostril of a patient. A septum divides the face piece into first and second flow paths such that the first flow path communicates with the first nare and the second flow path communicates with the second nare. A leading end of the first nare is configured to form a fluid barrier within a first nostril and facilitate only supplying an insufflation gas, via the first flow path, to the patient and prevent exhausting any exhaust gas, of the patient, through the first nostril. A leading end of the second nare is configured to facilitate collecting some of the exhaust gas, from the patient, via the second flow path as well as exhausting a remainder of the exhaust gas out through a second nostril of the patient.

20 Claims, 3 Drawing Sheets (56) References Cited

U.S. PATENT DOCUMENTS

| | | | |
|---|---|---|---|
| 2004/0045552 A1* | 3/2004 | Curti | A61M 16/0666 128/207.18 |
| 2004/0139973 A1* | 7/2004 | Wright | A61M 16/0666 128/207.18 |
| 2005/0066976 A1* | 3/2005 | Wondka | A61M 16/00 128/207.18 |
| 2006/0174889 A1* | 8/2006 | Noble | A61M 16/01 128/206.11 |
| 2011/0067708 A1* | 3/2011 | Doshi | A61M 15/08 128/848 |
| 2011/0214676 A1 | 9/2011 | Allum et al. | |
| 2011/0284001 A1 | 11/2011 | Tero | |
| 2012/0271187 A1* | 10/2012 | McNeill | A61M 16/085 600/532 |
| 2012/0304992 A1 | 12/2012 | Ratto et al. | |

\* cited by examiner

METHOD AND SYSTEM WITH DIVIDED CANNULA HAVING LOW OXYGEN FLOW RATE AND IMPROVED END-TIDAL $CO_2$ MEASUREMENT

This application claims the benefit of U.S. provisional application Ser. No. 61/792,007 filed Mar. 15, 2013.

FIELD OF THE INVENTION

The present invention relates to a new and improved divided nasal cannula which permits improvement in the amount of oxygen which is actually dissolved within the bloodstream of the patient, at a lower oxygen supply flow rate to the patient, and also improves collection and measurement of a substantially undiluted sample of the end-tidal carbon dioxide contained within the exhaled gases from the patient.

BACKGROUND OF THE INVENTION

As is well known in the art, a number of divided cannulas are currently available on the market which assist with both supplying a desired treatment or insufflation gas, such as oxygen, to the patient via a first insufflating nare of the nasal cannula and also facilitates detection of a desired exhaled gas, such as carbon dioxide, via a second sampling nare of the nasal cannula. U.S. Pat. Nos. 5,335,656 and 6,655,385 are examples of two currently known exemplary divided cannulas and the teachings and disclosures of both of those references are incorporated herein by reference in their entireties.

While the prior art designs provide a significant improvement over the prior art, there still remain a number of issues that need to be addressed. Specifically, it was discovered that with prior art cannulas, the amount of oxygen being supplied to the patient did not equal the amount of oxygen actually being absorbed into the bloodstream of the patient. In order to increase the oxygen level within the bloodstream, it was necessary to increase the supply of oxygen to the patient beyond the 'required' amount. It was also found that administering more oxygen to the patient typically resulted in greater dilution of the end-tidal exhalation gases. Such dilution adversely effects detection of the amount of end-tidal $CO_2$ within the end-tidal exhalation gases of the patient thereby skewing the accurate analysis.

While such nasal cannulas have perform relatively satisfactorily, there still is a need for improving collection of a substantially undiluted sample of the end-tidal exhaled gases, and detection of the amount of carbon dioxide contained in the end-tidal exhaled gases of the patient so that such reading more accurately reflects the actual amount of dissolved $CO_2$ contained within the bloodstream of the patient. In addition, a relatively low flow rate of oxygen, which adequately sustains the highest level of dissolved oxygen in the blood of the patient, is also desirable so as to minimize the effect that any excess oxygen, supplied to the patient, can have on the collected and measured end-tidal $CO_2$ gases during the time period that the patient is connected with the nasal cannula.

It is desirable to deliver supplemental oxygen to a patient in order to sustain a normal and desired level of dissolved oxygen within the bloodstream of the patient of 100 mmHg $PaO_2$ (e.g., the partial pressure of dissolved $O_2$). That is, the normal $PaO_2$ for a person breathing 21% oxygen (typically found in air) at sea level is 100 mmHg. Accordingly, in the event that the $PaO_2$ (i.e., partial pressure of dissolved $O_2$) of the patient drops below 100 mmHg, then it is necessary to supply supplementary oxygen to the patient in order to increase the $PaO_2$ of the patient to the desired level. Currently, a prior art divided cannula is utilized for supplying supplemental oxygen to the patient and such cannula typically has an oxygen flow rate of up to about 6 liters per minute.

SUMMARY OF THE INVENTION

Wherefore, it is an object of the present invention to overcome the above mentioned shortcomings and drawbacks associated with the prior art prior nasal cannulas and improve the collection of a substantially undiluted sample of the patient's end-tidal exhalation gases. This, in turn, leads to an improved detection of the amount of carbon dioxide contained in the end-tidal exhaled gases of the patient so that such reading more accurately reflects the actual partial pressure of $CO_2$ contained within the bloodstream of the patient. This, in turn, also minimizes flow of oxygen to the patient so that a majority of the oxygen, which is actually supplied to the patient, is eventually inhaled by and absorbed within the bloodstream of the patient.

Another object of the present invention is to divide the nostril of the patient into essentially first and second separate nasal cavities, with the first insufflation nasal cavity being substantially devoted to supplying oxygen to the patient while the second nasal cavity being substantially devoted to assisting with exhalation, and collection and detection of the carbon dioxide contained within the exhaust gases of the patient and thereby facilitate a more accurate measurement of the end-tidal $CO_2$ in the exhaust gases of the patient.

A further object of the present invention is to minimize the flow rate of the oxygen, which is supplied to the patient, while still ensuring that an adequate amount of oxygen is supplied to and inhaled by the patient so that such oxygen can be dissolved within the bloodstream of the patient to maintain the patient's bloodstream sufficiently saturated with oxygen.

Yet another object of the present invention is to minimize dilution of the exhaled gases of the patient, with any of the oxygen supplied by the insufflating nare of the nasal cannula, so as to provide an improved and more accuracy measurement of the end-tidal $CO_2$ contained within the exhaled gases of the patient.

Yet another object of the present invention is to either: (1) provide the insufflation nare with a one-way valve which only permits the flow of oxygen out through the one-way valve and into the nostril of the patient, during inhalation by the patient, but closes and adequately seals the outlet of the insufflating nare, during exhalation of the patient, so as to prevent any carbon dioxide from flowing into the outlet of the insufflating nare which is supplying oxygen to the patient, (2) provide the cannula with a fluid barrier which balances the pressure generated by the patient, during exhalation, with the resistance to flow of the supplied oxygen out through the opening(s), provided within the sidewall of the insufflating nare, so as to prevent, or minimize at the very least, any carbon dioxide from flowing into the outlet of the insufflating nare during exhalation of the patient, or (3) provide a mechanism of regulating/interrupting the flow of oxygen to the insufflating nare of the divided cannula so as to coincide with the breathing sequence, e.g., inhalation and exhalation, of the patient. That is, the flow of oxygen is only provided during inhalation by the patient but not during exhalation. U.S. Pat. Nos. 5,697,364 and 5,626,131 which relate to an electronic oxygen conservers that deliver oxygen, at the end of exhalation, and terminate oxygen delivery, at the beginning of inhalation, would be suitable for this and the teachings and disclosures of those references are incorporated herein by reference in their entireties.

A still further object of the present invention is to provide the insufflating nare with an annular or a peripheral member which is able to achieve an adequate perimeter nasal seal so that when the insufflating nare is received within the corresponding nostril of the patient, the perimeter nasal seal generally forms a seal with the skin or adjacent tissue of the nasal passage of the nostril and prevents any flow of room air into the nostril, past the perimeter nasal seal, and also prevents exhalation of any exhaust gases, from the patient, past the perimeter nasal seal.

Another object of the present invention is to ensure that the exterior sidewall or surface of the second sampling nare and the inwardly facing skin or adjacent tissue of the nasal passage of the nostril have a sufficient clearance therebetween so as to provide a substantially unobstructed exhalation passageway for the exhaust gases, including the carbon dioxide, of the patient during exhalation.

A still further object of the present invention is to obtain a less diluted sample of the end tidal $CO_2$, within the end-tidal exhalation gases exhausted by the patient, which more closely corresponds to and reflects the actual amount of carbon dioxide that is contained and dissolved within the bloodstream of the patient.

The present invention also relates to a nasal cannula comprising: an elongate face piece comprising first and second nares, and the first nare facilitates communication with a first nostril of a patient while the second nare facilitates communication with a second nostril of a patient; a septum dividing the face piece into first and second flow paths such that the first flow path communicating with the first nare and the second flow path communicating with the second nare; a leading end of the first nare being configured to form a fluid barrier within a first nostril of a patient to facilitate only supplying an insufflation gas, via the first flow path, to the patient and prevent exhausting any of an exhaust gas, from the patient, through the first nostril of the patient; and a leading end of the second nare being configured to facilitate collecting some of the exhaust gas, from the patient, via the second flow path as well as exhausting a remainder of the exhaust gas, from the patient, out through the second nostril of the patient.

The present invention also relates to a nasal cannula comprising: an elongate face piece comprising first and second nares, and the first nare facilitates communication with a first nostril of a patient while the second nare facilitates communication with a second nostril of the patient; a septum dividing the face piece into first and second flow paths such that the first flow path communicates with the first nare and the second flow path communicates with the second nare; a leading end of the first nare being configured to form a fluid barrier within the first nostril of the patient to facilitate only supplying an insufflation gas, via the first flow path, to the patient and prevent exhaust any of exhaust gas, from the patient, through the first nostril of the patient; at least one opening being formed in a sidewall of the first nare, and the at least one opening in the first nare permits the insufflating gas to collect and accumulate temporarily in a nasal region closely surrounding and adjacent the first nare, and reenter into the first nare, through the at least one opening, and be inhaled by the patient during inhalation by the patient; a leading end of the second nare being configured to facilitate collection of some of the exhaust gas, from the patient, via the second flow path as well as exhausting a remainder of the exhaust gas, from the patient, out through the second nostril of the patient; and a first opening being formed in a first end of the face piece while a second opening being formed in the opposite second end of the face piece, an oxygen supply tube being connected to the first opening while an end-tidal $CO_2$ detection tube being connected to the second opening, a second opposed end of the oxygen supply tube being connected to a source of an oxygen gas while a second opposed end of the end-tidal $CO_2$ detection tube being connected to a carbon dioxide monitoring device.

The present invention also relates to a method of improving measurement of end tidal $CO_2$ gas exhaled by a patient with a divided cannula which comprises an elongate face piece comprising first and second nares, and the first nare facilitates communication with a first nostril of the patient while the second nare facilitates communication with a second nostril of the patient; a septum dividing the face piece into first and second flow paths such that the first flow path communicating with the first nare and the first nostril and the second flow path communicating with the second nare and the second nostril; a leading end of the first nare being configured to form a fluid barrier within the first nostril of the patient to facilitate only supplying an insufflation gas, via the first flow path, to the patient and prevent exhausting any of exhaust gas, from the patient, through the first nostril of the patient; and a leading end of the second nare being configured to facilitate collecting some of the exhaust gas, from the patient, via the second flow path as well as exhausting a remainder of the exhaust gas, from the patient, out through a second nostril of the patient; the method comprising the steps of: dedicating the first nostril of the patient for solely supplying the insufflation gas to the patient and preventing exhausting any exhaust gas through the first nostril; and dedicating the second nostril of the patient for solely exhaling gas from the patient and sampling the end tidal $CO_2$ gas, exhaled by the patient, via the second nare

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
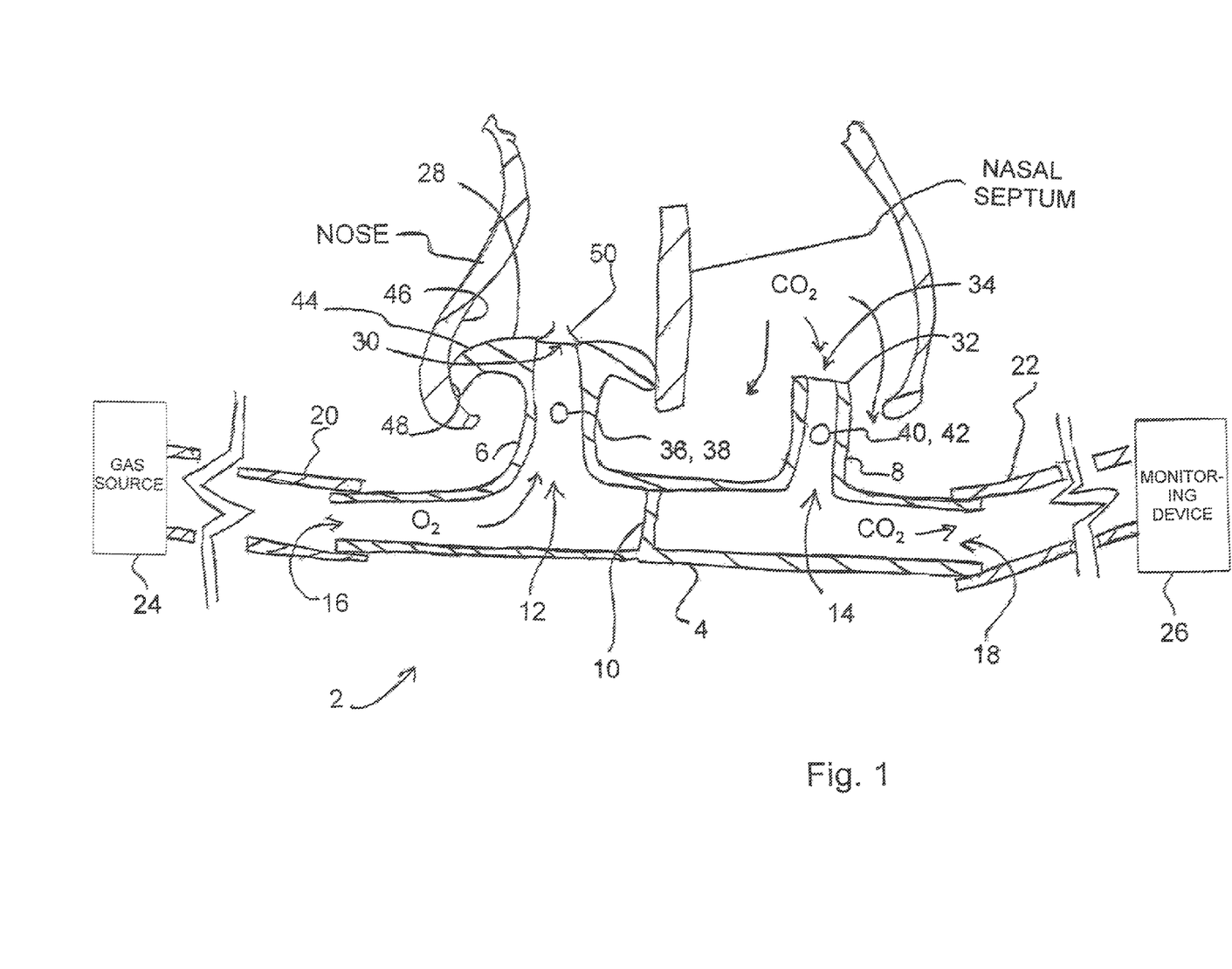
FIG. 1 is a diagrammatic cross-sectional view showing the improved divided cannula, according to the present invention, with the fluid barrier formed by a one-way valve being shown in an open position permitting fluid flow.
Figure 2:
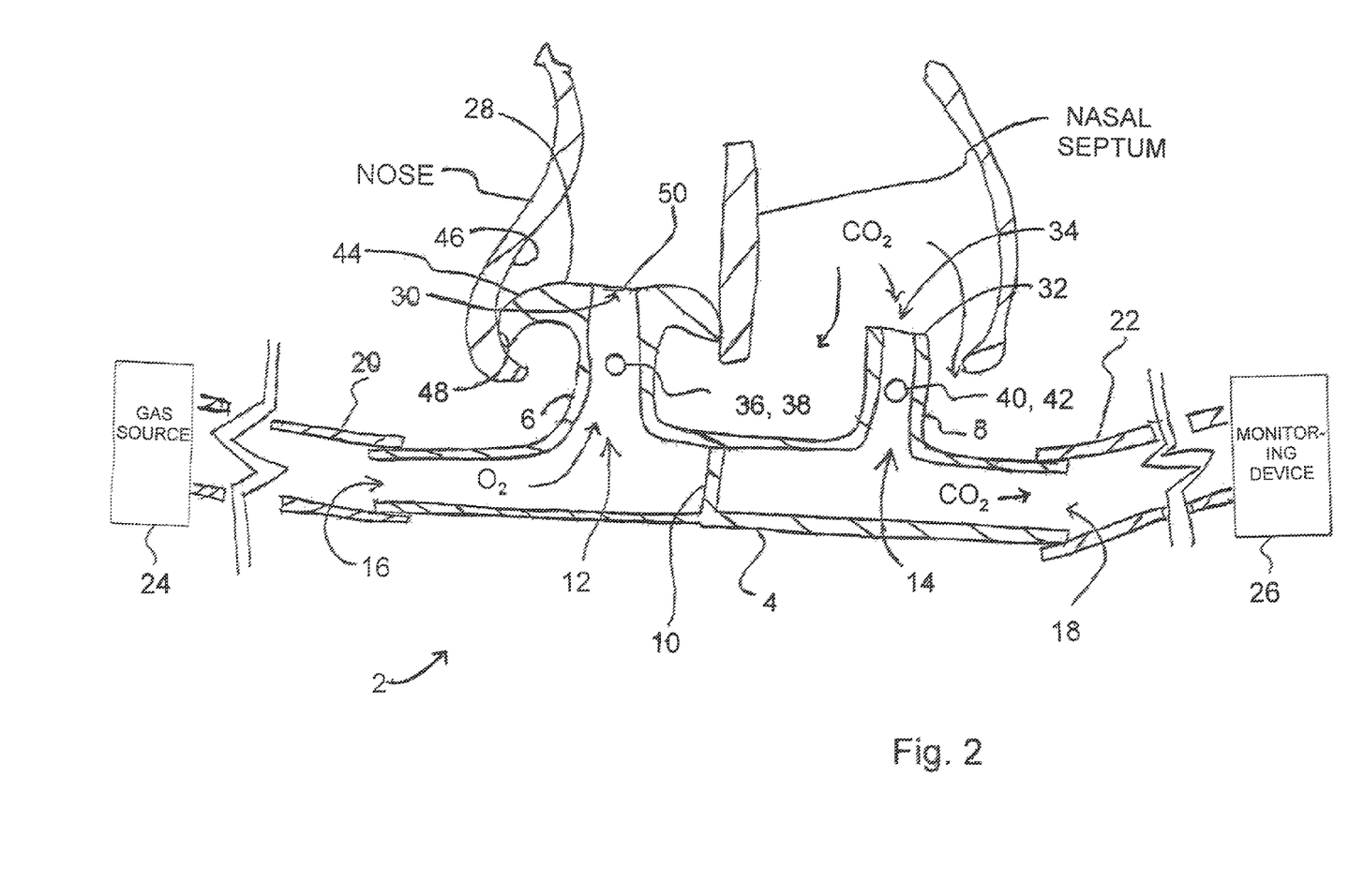
FIG. 2 is a diagrammatic cross-sectional view of the improved divided cannula, of FIG. 1, with the one-way valve being shown in a closed position prevention fluid flow.

Turning now to FIGS. 1 and 2, a brief description concerning the various components of the present invention will now be briefly discussed. As can be seen in this embodiment, the nasal cannula 2 generally comprises a generally tubular elongate face piece 4 having a first insufflating nare 6 and a second sampling nare 8, respectively, and a dividing septum 10 located therebetween. The dividing septum 10 is disposed and generally centered within the face piece 4, between a pair of respective passages 12 and 14 which facilitate communication with the respective first and second nares 6 and 8.

A first opening 16 is formed in a first end of the face piece 4 while a second opening 18 is formed in the opposite second end of the face piece 4. A first end of an oxygen supply tube 20 is connected to the first opening 16 of the face piece 4. A second opposed end of the oxygen supply tube 20 is connected to a source of an insufflating gas 24, such as oxygen. A first end of an end-tidal $CO_2$ detection tube 22 is connected to the second opening 18 of the face piece 4. A second opposed end of the end-tidal $CO_2$ detection tube 22 is connected to a commercial carbon dioxide monitoring device or unit 26 which, in turn, has or is connected to a vacuum pump or other means or mechanism for drawing an exhaled breath (exhalation gases) from the patient. The exhaled breath, generally containing carbon dioxide, is drawn into a conventional instrument that is capable of measuring the concentration of the carbon dioxide contained within the sampled gas. As the source of the insufflating gas 24 and the carbon dioxide monitoring device or unit 26 are both conventional and well known in the art, a further detailed discussion concerning the same is not provided.

As is conventional in the art, during use of the cannula 2, both insufflation with the insufflating gas, e.g., oxygen, and the monitoring of the carbon dioxide concentration, in the exhaled breath of the patient, occur simultaneously with one another. However, as noted above, this can lead to distorted readings in the measured end-tidal carbon dioxide of the patient, e.g., dilution of the amount of the carbon dioxide detected in the exhalation gases. Such dilution can occur when there is undesired mixing of either room air and/or excess insufflating gas with the exhalation gases from the patient. In addition, the carbon dioxide measuring device or unit 26, which typically employs varying amounts of suction or vacuum in order to obtain the exhalation gas sample to be analyzed, can significantly dilute the sample. Likewise, dilution can also occur when the tip 32 of the second sampling nare 8 engages or is drawn into contact with the adjacent skin or tissue of the nasal passage. This causes either a partial, or possibly a total, occlusion of the inlet 34 of the sampling nare 8 thereby restricting, or even possibly preventing, adequate sampling of the carbon dioxide concentration in the exhaled gases of the patient.

As is known in the art, in order to minimize this possibility from occurring, one or more very small holes, or openings, shown as 36 and 38 or 40 and 42, are formed in the sidewall of both the insufflating nare 6 and/or the sampling nare 8.

Such openings 40 and 42, in the sampling nare 8, preventing an undesirable and unnecessary level of suction, at the inlet 34 of the tip 32, from developing and drawing the tip 32 of the sampling nare 8 into engagement with the skin or nasal tissue and thereby possibly occluding the inlet 34 of the sampling nare 8. The openings 40 and 42 in the sampling nare 8 are large enough to prevent sufficient suction from developing at the tip 32 so as to draw in mucosal secretions and/or attach the tip 32, by suction, to the soft mucosal tissue, while still facilitate adequate sampling of a substantially undiluted sample of the exhalation gases from the patient and thereby provide a reliable end-tidal carbon dioxide measurement. Likewise, excessively large openings 40 and 42 may undesirably dilute the exhalation gas sample of the patient with room air and/or excess insufflation gas. Preferably the openings 40 and 42 in the sampling nare 8 have a diameter of between about 0.05 to about 0.07 inches.

The openings 36 and 38 in the insufflating nare 6, on the other hand, permit oxygen to be exhausted out through such openings 36 and 38 and temporarily collect and accumulate within a nasal region closely adjacent and surrounding the insufflating nare 6, when the one-way valve 50 of the insufflating nare 6 is in its closed position and/or the patient is exhaling. As soon as the one-way valve 50 opens, during inhalation by the patient, such openings 36 and 38 in the insufflating nare 6 permit the vented oxygen, which temporarily collects and accumulates in the nasal region closely surrounding and adjacent the insufflating nare 6, to reenter into the insufflating nare 6, through the openings 36 and 38, and eventually be inhaled by the patient and thereby maximize the supply of oxygen to the patient.

The openings 36 and 38 in the insufflating nare 6 are large enough to exhaust the supplied oxygen at sufficiently low flow rates so that such oxygen can exhaust, collect and accumulated in the nasal region closely adjacent the insufflating nare 6. Likewise, excessively large openings 36 and 38 may undesirably dilute the inhaled supply gas, with room air, thereby decreasing the amount of oxygen that is eventually supplied to, inhaled by and eventually dissolved within the bloodstream of the patient. Preferably, the size of the openings 36 and 38 in the insufflating nare 6 are between about 0.05 to about 0.07 inches.

It is to be appreciated that either larger or smaller openings, or possibly a single opening, may be provided in each of the insufflating and/or sampling nares 6, 8 in order to suit a particular needed, without departing from the spirit and the scope of the present invention and without any undue experimentation.

As shown in FIG. 1 the insufflating nare 6 is provided with a peripheral sealing member 44 which snugly engages with and seals against the inwardly facing skin or adjacent tissue of the nasal passage 46 of the nostril of the patient, once the insufflating nare 6 is properly located within the nostril, thereby forming a perimeter nasal seal 48. That is, according to this embodiment, the leading end of the insufflating nare 6 has an inverted mushroom shape head which is sized, shaped and configured so as to intimately and snugly engage with the inwardly facing skin or adjacent tissue of the nasal passage 46 of the nostril of the patient and thereby form the perimeter nasal seal 48. Such perimeter nasal seal 48 generally prevents, or minimizes, at the very least, exhalation of any exhaust gases, from the patient and also generally prevents, or minimizes at the very least, inhalation of any room air into that nostril past the perimeter nasal seal 48.

It is to be appreciated that the perimeter nasal seal 48 can be formed by a variety of other types of configurations. The important aspect of the perimeter nasal seal 48 is that it minimizes the flow into and out of the nostril, past the perimeter nasal seal 48 of the insufflating nare 6, so that the nostril which contains the insufflating nare 6, is essentially a dedicated insufflation nostril which only permits the supply of the insufflating gas, such as oxygen, to the patient. Preferably, the design of the perimeter nasal seal 48 will be such that it does not cause any discomfort to the patient during prolonged or extended use.

In addition, a thin and flexible one-way valve 50 covers and generally seals the outlet 30 of the insufflating nare 6 to further assist with converting the nostril, which contains the insufflating nare 6, into a dedicated insufflation nostril which only permits the supply of the insufflating gas, such as oxygen, to the patient. The one-way valve 50 generally comprises a sealed opening which is provided with at least one slit, and possible a plurality of slits, which allows the one-way valve 50 to open when there is a suitable pressure differential on opposed sides of the one-way valve 50. The one-way valve 50 of the insufflating nare 6 is normally biased into a closed position (see FIG. 2) so as to prevent any exhaust gases, during exhalation of the patient, from flowing into the outlet 30 of the insufflating nare 6 while, at the same time, rapidly and easily open (see FIG. 1), during inhalation of the patient, to allow the insufflating gas, such as oxygen, to flow readily into the nostril and be inhaled by the patient in a conventional manner.

The second sampling nare 8, which is received by the other nostril, is sized to be significantly smaller than the respective nostril so as to permit easy exhalation of all of the exhaust gases, of the patient, out through a single nostril of the patient. That is, the nostril which contains the second sampling nare 8 becomes a dedicated exhalation nostril for exhausting all of the exhaust gases from the patient and for measuring the end tidal $CO_2$ of the patient. That is, preferably the transverse cross-sectional area of the second sampling nare 8 occupies approximately 50% or less than the total transverse cross-sectional area of the respective nostril so as to provide a sufficient open and unobstructive cross sectional area to facilitate exhausting all of the exhaust gases of the patient through a single nostril while still facilitating accurate measurement of the end tidal $CO_2$ of the patient.

Figure 3:
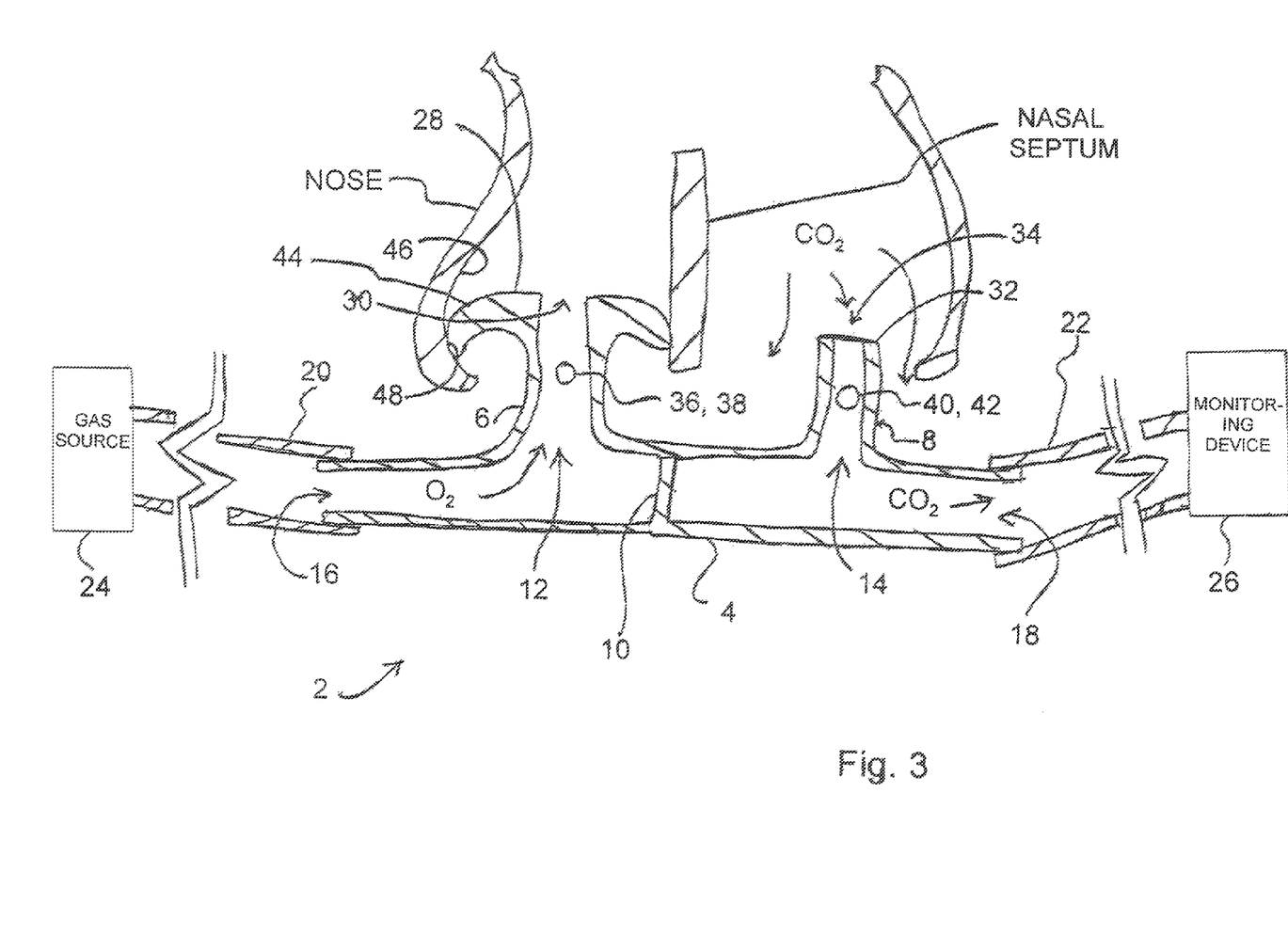
FIG. 3 is a diagrammatic cross-sectional view showing the improved divided cannula, according to the present invention, with the fluid barrier created by pressure.

Turning now to FIG. 3, a brief description concerning this embodiment will now be discussed. As this embodiment is substantially identical to the previous embodiment discussed with respect to FIGS. 1 and 2, only the differences between this second embodiment and the previous embodiment will be discussed in detail.

The primary difference between this second embodiment in the previous embodiment is the elimination of the one-way valve 50. According to this embodiment, the flow of fluid in an undesired flow direction is prevented by a pressure barrier instead of a physical valve. That is, the pressure based fluid barrier is created by a pressure barrier formed when the pressure of the exhalation gases, generated by the patient during exhalation, is balanced with the pressure of the supplied insufflating gas, e.g., oxygen, the resistance to flow of the supplied insufflating gas out through the opening(s) 36 and 38, provided within the sidewall of the insufflating nare 6. Due to such balancing, the pressure of the exhalation gases essentially prevent any insufflating gas, e.g., oxygen, from being exhausted out through the outlet 30 of the insufflating nare 6 during exhalation by the patient. Such balancing also essentially prevents any insufflating gas from exiting through the outlet 30 and also prevents any exhaled gases from entering into the outlet 30.

It is to be appreciated that either embodiment may incorporate a conserver as the source of the insufflating gas 24 for supplying the insufflating gas. In such event, the insufflating gas is supplied, via the conserver, only upon inhalation and the conserver includes a conventional mechanism for regulating/interrupting the flow of the insufflating gas, e.g., oxygen, to the divided cannula so as to coincide with the breathing sequence, e.g., inhalation and exhalation, of the patient. That is, the flow of oxygen is only provided during inhalation by the patient but not during exhalation of the patient. As is conventional in the art, the conserver determines when the patient is exhaling and thus determines when oxygen is necessary for inhalation by the patient.

As is well known in the art, such conserver commences delivers the insufflating gas, e.g., oxygen, only at the end of exhalation, and terminates delivery of the insufflating gas at the end of inhalation. This alternates the fluid pressure at the outlet 30 of insufflating nare 6. This alternating fluid pressure, at the outlet 30 of the insufflating nare 6, also may allow for the elimination of the openings 36, 38 while still providing a fluid barrier.

It is contemplated that the divided cannula, according to the present invention, is able to reduce the oxygen flow rate to about 3 liters per minute while still generally being able to achieve an adequate amount of dissolved oxygen within the bloodstream of the patient, e.g., achieve a desired partial pressure of dissolved oxygen within the bloodstream of 100 mmHg. In addition, the divided cannula, according to the present invention, is able to obtain a substantially undiluted sample of the exhaled end tidal $CO_2$ gases of the patient which, in turn, translates into a more accurate measurement of the actual partial pressure of the dissolved carbon dioxide within the bloodstream of the patient. That is, for a patient in which partial pressure of the dissolved carbon dioxide within the bloodstream is 40 mmHg of $CO_2$, the divided cannula, according to the present invention, is typically able to measure about 35-38 mmHg of $CO_2$. As such, the divided cannula, according to the present invention, has two major benefits, the first being a more accurate detection of the actual carbon dioxide which is dissolved within the bloodstream of the patient and the second being the supply a reduced amount of an insufflating gas, such as oxygen, to the patient while still achieving adequate oxygen saturation of the patient.

While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of the terms "including," "comprising," or "having" and variations thereof herein is meant to encompass the items listed thereafter and equivalents thereof as well as additional items and features and only the terms "consisting of" and "consisting only of" are to be construed in the limitative sense.

Wherefore, I claim:

1. A nasal cannula comprising:
    an elongate face piece comprising first and second nares, and the first nare facilitates communication with a first nostril of a patient while the second nare facilitates communication with a second nostril of the patient;
    a septum dividing the face piece into first and second flow paths such that the first flow path communicating with the first nare and the second flow path communicating with the second nare;
    a leading end of the first nare comprising a peripherally extending sealing member which is adapted to engage with adjacent tissue of a nasal passage of the first nostril to form a fluid barrier within the first nostril of the patient to facilitate only supplying an insufflation gas, via the first flow path, to the patient and prevent exhausting any of an exhaust gas, from the patient, past the fluid barrier, the first nare and the peripherally extending sealing member being integrally formed as a single piece from a same material; and a leading end of the second nare being configured to facilitate collecting some of the exhaust gas, from the patient, via the second flow path as well as exhausting a remainder of the exhaust gas, from the patient, out through the second nostril of the patient.

2. The nasal cannula according to claim 1, wherein the nasal cannula is tubular and the septum is disposed generally centered within the face piece, between a pair of respective flow passages, which facilitate communication with the respective first and second nares.

3. The nasal cannula according to claim 2, wherein a first opening is formed in a first end of the face piece while a second opening is formed in an opposite second end of the face piece, and an oxygen supply tube is connected to the first opening at a first end of the oxygen supply tube while an end-tidal $CO_2$ detection tube is connected to the second opening at a first end of the end-tidal $CO_2$ detection tube, a second opposed end of the oxygen supply tube is connected to a source of an oxygen gas while a second opposed end of the end-tidal $CO_2$ detection tube is connected to a carbon dioxide monitoring device.

4. The nasal cannula according to claim 1, wherein a first opening is formed in a first end of the face piece while a second opening is formed in an opposite second end of the face piece, and a supply tube is connected to the first opening, while a detection tube is connected to the second opening.

5. The nasal cannula according to claim 4, wherein the supply tube and the detection tube each comprise a first end connected to the face piece and a second end opposite the face piece, wherein the second end of the supply tube is connected to a source of an insufflating gas while the second end of the detection tube is connected to a carbon dioxide monitoring device.

6. The nasal cannula according to claim 1, wherein the first nare extends along an axis, at least one opening is formed in a sidewall of the first nare and the at least one opening is axially located upstream from the peripherally extending sealing member with respect to a flow of the insufflation gas to the patient.

7. The nasal cannula according to claim 6, wherein the at least one opening in the first nare has a diameter of between 0.05 and 0.07 inches and the at least one opening is axially located between the peripherally extending sealing member and an opposite end of the first nare that is opposite from the leading end of the first nare.

8. The nasal cannula according to claim 6, wherein the at least one opening in the first nare permits the insufflating gas to collect and accumulate temporarily in a nasal region closely surrounding and adjacent the first nare, so that the accumulated insufflating gas may then reenter into the first nare, through the at least one opening, and be inhaled by the patient and maximize the insufflating gas delivered to the patient.

9. The nasal cannula according to claim 8, wherein the at least one opening in the second nare has a diameter of between 0.05 and 0.07 inches.

10. The nasal cannula according to claim 6, wherein the first nare has a one-way valve which, when open, permits the flow of the insufflating gas into the first nostril of the patient, and when closed, prevents the flow of the exhaust gas from the patient into the first nare.

11. The nasal cannula according to claim 1, wherein at least one opening is formed in a sidewall of the second nare, and the at least one opening in the sidewall of the second nare prevents an undesirable level of suction from developing at an inlet of a tip of the second nare, thereby preventing drawing the tip of the second nare into contact with nasal tissue, and preventing occlusion of the inlet of the second nare.

12. The nasal cannula according to claim 1, wherein the peripherally extending sealing member which snugly engages with the adjacent tissue of the nasal passage of the first nostril of the patient, once the first nare is located therein, forms a perimeter nasal seal.

13. The nasal cannula according to claim 12, wherein the peripherally extending sealing member is located at the leading end of the first nare and has an inverted mushroom shape head which is sized, shaped and configured so as to intimately and snugly engage with the adjacent tissue of the nasal passage of the first nostril of the patient and thereby form a perimeter nasal seal therewith which prevents passage of any exhaust gas, from the patient, past the perimeter nasal seal and also prevents inhalation of any room air via the first nostril past the perimeter nasal seal.

14. The nasal cannula according to claim 1, wherein a flexible one-way valve covers and seals an outlet of the first nare to assist with converting the first nostril, which receives the first nare, into a dedicated insufflation nostril which only permits the supply of the insufflating gas to the patient.

15. The nasal cannula according to claim 14, wherein the one-way valve comprises a sealed opening which is provided with at least one slit, and the one-way valve of the first nare is normally biased into a closed position so as to prevent any exhaust gas, during exhalation of the patient, from flowing into the outlet of the first nare while, during inhalation of the patient, allowing the insufflating gas to flow past the one-way valve into the first nostril and be inhaled by the patient.

16. The nasal cannula according to claim 1, wherein the second nare is sized to be smaller than the second nostril so as to permit exhalation of the exhaust gases, of the patient, via the second nostril of the patient which receives the second nare.

17. The nasal cannula according to claim 16, wherein the second nare is adapted to be received within the second nostril of the patient such that the second nostril is a dedicated sampling nostril for exhausting the exhaust gas from the patient and for measuring the end tidal $CO_2$ of the patient, and the second nare is sized such that a transverse cross-sectional area of the second nare occupies approximately 50% or less than a total transverse cross-sectional area of the second nostril to facilitate open and unobstructed exhausting of the exhaust gases of the patient while still facilitating measurement of the end tidal $CO_2$ of the patient.

18. A nasal cannula comprising:
an elongate face piece comprising first and second nares, and the first nare defines an axis and facilitates communication with a first nostril of a patient while the second nare facilitates communication with a second nostril of the patient;
a septum dividing the face piece into first and second flow paths such that the first flow path communicates with the first nare and the second flow path communicates with the second nare;

a leading end of the first nare comprises a radially extending sealing member which is configured to form a fluid barrier within the first nostril of the patient to facilitate only supplying an insufflation gas, via the first flow path, to the patient and prevent exhausting any of an exhaust gas, from the patient, past the fluid barrier;

at least one opening being formed in a sidewall of the first nare and axially located between the radially extending sealing member and another end of the first nare opposite the leading end of the first nare, and the at least one opening in the first nare permits the insufflating gas to collect and accumulate temporarily in a nasal region closely surrounding and adjacent the first nare, and reenter into the first nare, through the at least one opening, and be inhaled by the patient during inhalation by the patient;

a leading end of the second nare being configured to facilitate collection of some of the exhaust gas, from the patient, via the second flow path as well as exhausting a remainder of the exhaust gas, from the patient, out through the second nostril of the patient; and a first opening being formed in a first end of the face piece while a second opening being formed in an opposite second end of the face piece, an oxygen supply tube being connected to the first opening at a first end of the oxygen supply tube while an end-tidal $CO_2$ detection tube being connected at a first end of the end-tidal $CO_2$ detection tube to the second opening, a second end of the oxygen supply tube opposite from the first opening of the face piece being connected to a source of an oxygen gas while a second end of the end-tidal $CO_2$ detection tube opposite from the second opening of the face piece being connected to a carbon dioxide monitoring device.

19. The nasal cannula according to claim 18, wherein the first nare has a one-way valve which, when open, permits a flow of the insufflating gas into the first nostril of the patient, and when closed, prevents a flow of exhaust gases into the first nare, and at least one opening is formed in a sidewall of the second nare, and the at least one opening in the second nare prevents an undesirable level of suction, at an inlet of the second nare, from developing and drawing the inlet of the second nare into nasal tissue and occluding the inlet of the second nare.

20. A method of improving measurement of end tidal $CO_2$ gas exhaled by a patient with a divided cannula which comprises an elongate face piece comprising first and second nares, and the first nare facilitates communication with a first nostril of the patient while the second nare facilitates communication with a second nostril of the patient; a septum dividing the face piece into first and second flow paths such that the first flow path communicating with the first nare and the first nostril and the second flow path communicating with the second nare and the second nostril; a leading end of the first nare comprising a peripherally extending sealing member which engages with adjacent tissue of a nasal passage of the first nostril to form a fluid barrier within the first nostril of the patient to facilitate only supplying an insufflation gas, via the first flow path, to the patient and prevent exhausting any of exhaust gas, from the patient, past the fluid barrier, the first nare and the peripherally extending sealing member being integrally formed as a single piece from a same material; and a leading end of the second nare being configured to facilitate collecting some of the exhaust gas, from the patient, via the second flow path as well as exhausting a remainder of the exhaust gas, from the patient, out through a second nostril of the patient; the method comprising the steps of:

dedicating the first nostril of the patient for solely supplying the insufflation gas to the patient and preventing exhausting any exhaust gas past the fluid barrier; and dedicating the second nostril of the patient for solely exhaling gas from the patient and sampling the end tidal $CO_2$ gas, exhaled by the patient, via the second nare.

* * * * *